United States Patent [19]

Lin et al.

[11] Patent Number: 5,693,107
[45] Date of Patent: Dec. 2, 1997

[54] FUEL COMPOSITIONS COMPRISING HYDANTOIN-CONTAINING POLYETHER ALCOHOL ADDITIVES

[75] Inventors: Jiang-Jen Lin; Pen-Chung Wang; Sarah Louise Weaver, all of Houston, Tex.

[73] Assignee: Shell Oil Company, Houston, Tex.

[21] Appl. No.: 692,560

[22] Filed: Aug. 6, 1996

Related U.S. Application Data

[60] Continuation of Ser. No. 447,368, May 23, 1995, abandoned, which is a division of Ser. No. 308,712, Sep. 19, 1994, Pat. No. 5,489,315.

[51] Int. Cl.$^6$ .................................................. C10L 1/22
[52] U.S. Cl. .................................................. 44/342
[58] Field of Search .................................................. 44/342

[56] References Cited

U.S. PATENT DOCUMENTS

| | | |
|---|---|---|
| 3,438,757 | 4/1969 | Honnen et al. |
| 3,574,576 | 4/1971 | Honnen et al. |
| 3,631,221 | 12/1971 | Batzer et al. .................. 548/319.1 |
| 3,679,681 | 7/1972 | Habermeier et al. |
| 3,753,670 | 8/1973 | Strang et al. |
| 3,756,793 | 9/1973 | Robinson. |
| 3,821,098 | 6/1974 | Garratt et al. |
| 3,882,137 | 5/1975 | Habermeier et al. |
| 3,893,979 | 7/1975 | Wolf et al. |
| 3,894,038 | 7/1975 | Habermeier et al. |
| 3,928,298 | 12/1975 | Wolf et al. |
| 3,932,176 | 1/1976 | Habermeier et al. |
| 4,038,277 | 7/1977 | Habermeier et al. |
| 4,160,648 | 7/1979 | Lewis et al. |
| 4,161,594 | 7/1979 | Batzer et al. .................. 548/319.1 |
| 4,191,537 | 3/1980 | Lewis et al. |
| 4,231,759 | 11/1980 | Udelhofen et al. |
| 4,236,020 | 11/1980 | Lewis et al. |
| 4,270,930 | 6/1981 | Campbell et al. |
| 4,288,612 | 9/1981 | Lewis et al. |
| 4,612,335 | 9/1986 | Cuscurida et al. |
| 4,810,261 | 3/1989 | Sung et al. |
| 4,852,993 | 8/1989 | Sung et al. |
| 4,881,945 | 11/1989 | Buckley, III. |
| 4,883,826 | 11/1989 | Marugg et al. |
| 4,936,868 | 6/1990 | Johnson. |
| 4,968,321 | 11/1990 | Sung et al. |
| 4,973,414 | 11/1990 | Nerger et al. |
| 4,985,047 | 1/1991 | Sung et al. |
| 5,061,291 | 10/1991 | Sung. |
| 5,100,907 | 3/1992 | Hall et al. .................. 548/319.1 |
| 5,123,932 | 6/1992 | Rath et al. |
| 5,147,414 | 9/1992 | Powers, III et al. |

Primary Examiner—Jerry D. Johnson

[57] ABSTRACT

The present invention is directed to the use of hydantoin-containing polyether alcohols as additives in a gasoline composition. The invention is also directed to the use of these compounds for decreasing intake valve deposits, controlling octane requirement increases and reducing octane requirement. The invention is further directed to hydantoin-containing compounds.

33 Claims, No Drawings

FUEL COMPOSITIONS COMPRISING HYDANTOIN-CONTAINING POLYETHER ALCOHOL ADDITIVES

This is a continuation of application Ser. No. 08/447,368, filed May 23, 1995, now abandoned which is a division of application Ser. No. 08/308,712, filed Sep. 19, 1994 now U.S. Pat. No. 5,489,315.

FIELD OF THE INVENTION

The present invention relates to the use of hydantoin-containing polyether alcohol compounds as additives in fuel compositions and the use of those compounds to decrease intake octane requirement. The present invention further relates to two classes of hydantoin-containing polyether alcohol compounds.

BACKGROUND OF THE INVENTION

The accumulation of deposits on the intake valves of internal combustion engines presents a variety of problems. The accumulation of such deposits is characterized by overall poor driveability including hard starting, stalls, and stumbles during acceleration and rough engine idle.

Many additives are known which can be added to hydrocarbon fuels to prevent or reduce deposit formation, or remove or modify formed deposits, in the combustion chamber and on adjacent surfaces such as intake valves, ports, and spark plugs. Continued improvements in the design of internal combustion engines, e.g., fuel injection and carburetor engines, bring changes to the environment of such engines thereby creating a continuing need for new additives to control the problem of inlet system deposits and to improve driveability which can be related to deposits.

It would be an advantage to have fuel compositions which would reduce the formation of deposits and modify existing deposits that are related to octane requirement increase and poor driveability in modern engines which burn hydrocarbon fuels.

SUMMARY OF THE INVENTION

The present invention is directed to the use of hydantoin-containing polyether alcohols as additives in fuel compositions comprising a major amount of a mixture of hydrocarbons in the gasoline boiling range and a minor amount of one or more hydantoin-containing polyether alcohol compounds of Formula I:

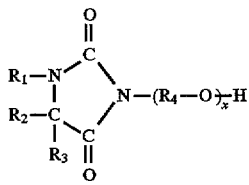
(I)

wherein $R_1$ is selected from the group consisting of hydrocarbyl of 1 to 100 carbon atoms, substituted hydrocarbyl of 1 to 100 carbon atoms and polyoxyalkylene alcohol of 2 to 200 carbon atoms; $R_2$ and $R_3$ are each independently selected from the group consisting of hydrogen, hydrocarbyl of 1 to 100 carbon atoms and substituted hydrocarbyl of 1 to 100 carbon or $R_2$ and $R_3$ taken together with the carbon atom to which they are connected form a cyclic group of 4 to 100 carbon atoms; each $R_4$ is independently selected from the group consisting of hydrocarbyl of 2 to 100 carbon atoms and substituted hydrocarbyl of 2 to 100 carbon atoms; and x is from 1 to 50;

or a minor amount of one or more of the hydantoin-containing polyether alcohol compounds of Formula II:

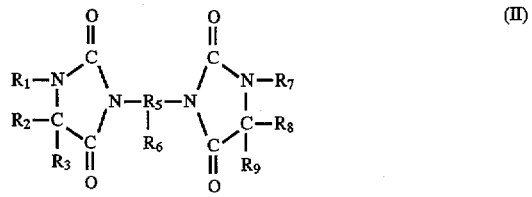
(II)

wherein $R_1$ and $R_7$ are each independently selected from the group consisting of hydrocarbyl of 1 to 100 carbon atoms, substituted hydrocarbyl of 1 to 100 carbon atoms and polyoxyalkylene alcohol of 2 to 200 carbon atoms; $R_6$ is selected from the group consisting of hydrogen, hydrocarbyl of 1 to 100 carbon atoms, substituted hydrocarbyl of 1 to 100 carbon atoms and polyoxyalkyl of formula:

$$-O-R_{10}$$ (III)

wherein $R_{10}$ is selected from the group consisting of hydrocarbyl of 1 to 100 carbon atoms, substituted hydrocarbyl of 1 to 100 carbon atoms and polyoxyalkylene alcohol of 2 to 200 carbon atoms with the proviso that when both $R_1$ and $R_7$ are not polyoxyalkylene alcohol, $R_6$ must be polyoxyalkyl wherein $R_{10}$ is polyoxyalkylene alcohol of 2 to 200 carbon atoms; $R_5$ is selected from the group consisting of hydrocarbyl of 1 to 100 carbon atoms and substituted hydrocarbyl of 1 to 100 carbon atoms; $R_2$, $R_3$, $R_8$ and $R_9$ are each independently selected from the group consisting of hydrogen, hydrocarbyl of 1 to 100 carbon atoms and substituted hydrocarbyl of 1 to 100 carbon atoms or $R_2$ and $R_3$ and/or $R_8$ and $R_9$ can each independently be taken together with the carbon atom to which they are connected to form a cyclic group of 4 to 100 carbon atoms.

The invention is also directed to the use of these hydantoin-containing polyether alcohols for decreasing intake valve deposits, controlling octane requirement increases and reducing octane requirement. The invention is further directed to two classes of hydantoin-containing polyether alcohol compounds.

DESCRIPTION OF THE PREFERRED EMBODIMENTS

COMPOUNDS

The compounds of the present invention, broadly expressed as hydantoin-containing polyether alcohols, are new additives useful for hydrocarbon fuels, e.g., fuels in the gasoline boiling range, for preventing deposits in engines. These compounds are also proposed for controlling octane requirement increases and reducing octane requirement. The compounds produce very little residue and are miscible with carriers and other detergents. Non-limiting illustrative embodiments of the compounds useful as additives in the instant invention include those of Formula I:

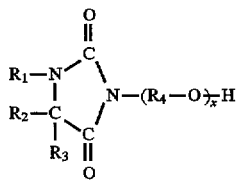
(I)

In Formula I, $R_1$ is selected from the group consisting of hydrocarbyl of 1 to 100 carbon atoms, substituted hydrocarbyl of 1 to 100 carbon atoms and polyoxyalkylene alcohol of 2 to 200 carbon atoms.

As used herein, the term "hydrocarbyl" represents a radical formed by the removal of one or more hydrogen atoms from a carbon atom of a hydrocarbon (not necessarily the same carbon atom). Useful hydrocarbyls are aliphatic, aromatic, substituted, unsubstituted, acyclic or cyclic. Preferably, the hydrocarbyls are aryl, alkyl, alkenyl or cycloalkyl and are straight-chain or branched-chain. Representative hydrocarbyls include methyl, ethyl, butyl, pentyl, methylpentyl, hexenyl, ethylhexyl, dimethylhexyl, octamethylene, octenylene, cyclooctylene, methylcyclooctylene, dimethylcyclooctyl, isooctyl, dodecyl, hexadecenyl, octyl, eicosyl, hexacosyl, triacontyl and phenylethyl. As noted, the hydrocarbyls utilized may be substituted. As used herein, the term "substituted hydrocarbyl" refers to any "hydrocarbyl" which contains a functional group such as carbonyl, carboxyl, nitro, amino, hydroxy (e.g. hydroxyethyl), oxy, cyano, sulfonyl, and sulfoxyl. The majority of the atoms, other than hydrogen, in substituted hydrocarbyls are carbon, with the heteroatoms (i.e., oxygen, nitrogen, sulfur) representing only a minority, 33% or less, of the total non-hydrogen atoms present.

When $R_1$ is hydrocarbyl or substituted hydrocarbyl, $R_1$ is preferably selected from hydrocarbyl of 1 to 50 carbon atoms and substituted hydrocarbyl of 1 to 50 carbon atoms. In the more preferred embodiments, $R_1$ is hydrocarbyl. Preferably when $R_1$ is hydrocarbyl, it is hydrocarbyl selected from alkyl of 1 to 20 carbon atoms, cyclic alkyl of 4 to 20 carbon atoms and aromatic of 6 to 20 carbon atoms, more preferably alkyl of 1 to 10 carbon atoms, cyclic alkyl of 5 to 10 carbon atoms and aromatic of 6 to 10 carbon atoms and most preferably alkyl of 1 to 5 carbon atoms, cyclic alkyl of 5 to 8 carbon atoms and aromatic of 6 carbon atoms. In the most preferred embodiments, when $R_1$ is hydrocarbyl, it is selected from alkyl of 1 to 20 carbon atoms and more preferably alkyl of 1 to 10 carbon atoms, especially methyl. When $R_1$ is hydrocarbyl of a relatively high number of carbon atoms, i.e., greater than about 50 carbon atoms, $R_1$ will be represented by polymeric hydrocarbyls derived from polyisobutylene, polybutene, polypropylene or polyalphaolefins.

When $R_1$ is polyoxyalkylene alcohol of 2 to 200 carbon atoms, $R_1$ is preferably polyoxyalkylene alcohol of Formula IV:

—(R$_{11}$—O)$_y$H     (IV)

wherein each $R_{11}$ is independently selected from the group consisting of hydrocarbyl, as defined hereinbefore, of 2 to 100 carbon atoms and substituted hydrocarbyl, as defined hereinbefore, of 2 to 100 carbon atoms and y is from 1 to 50. Preferably, each $R_{11}$ is independently selected from hydrocarbyl of 2 to 100 carbon atoms. When $R_{11}$ is hydrocarbyl of a relatively high number of carbon atoms, i.e., greater than about 50 carbon atoms, each will be represented by polymeric hydrocarbyls derived from polyisobutylene, polybutene, polypropylene or poly-alphaolefins. More preferably, each $R_{11}$ is independently selected from hydrocarbyl of 2 to 20 carbon atoms. Particularly preferred compounds are those in which each $R_{11}$ is independently selected from alkyl of 2 to 20 carbon atoms, more preferably alkyl of 2 to 4 carbon atoms, especially alkyl of 4 carbon atoms.

Particularly preferred compounds of Formula I are those in which when $R_1$ is polyoxyalkylene alcohol, $R_{11}$ is hydrocarbyl (geminal or vicinal) of Formula V or Formula VI:

wherein $R_{12}$, $R_{13}$ and $R_{14}$ are each independently selected from hydrogen, hydrocarbyl, as defined hereinbefore, of 1 to 98 carbon atoms and substituted hydrocarbyl, as defined hereinbefore, of 1 to 98 carbon atoms. Preferably $R_{12}$, $R_{13}$ and $R_{14}$ are independently selected from hydrogen, hydrocarbyl of 1 to 18 carbon atoms and substituted hydrocarbyl of 1 to 18 carbon atoms. $R_{13}$ and $R_{12}$, or in the alternative $R_{12}$ and $R_{14}$, may be taken together to form a divalent linking hydrocarbyl group of 3 to 12 carbon atoms.

The most preferred compounds of Formula I are those in which when $R_1$ is polyoxyalkylene, $R_{11}$ is hydrocarbyl as represented by Formula V above wherein each $R_{14}$ is hydrogen and each $R_{12}$ is independently selected from hydrogen, alkyl of 1 to 18 carbon atoms and oxy-substituted hydrocarbyl of 1 to 18 carbon atoms, particularly those compounds where each $R_{14}$ is hydrogen and each $R_{12}$ is independently hydrogen or alkyl of 1 to 2 carbon atoms, especially those compounds where each $R_{14}$ is hydrogen and each $R_{12}$ is alkyl of two carbon atoms.

When $R_{12}$ is oxy-substituted hydrocarbyl of 1 to 18 carbon atoms, $R_{12}$ is preferably an alkoxy-substituted alkylene of 1 to 18 carbon atoms or an aryloxy-substituted alkylene of 1 to 18 carbon atoms. Particularly preferred alkoxy-substituted alkylene groups include ethylhexyleneoxymethylene, isopropoxymethylene, butoxymethylene and mixtures thereof. Particularly preferred aryl-substituted alkylene groups include nonylphenoxymethylene, phenoxymethylene and mixtures thereof.

In Formula IV above, y is from 1 to 50, preferably from 1 to 40, and even more preferably from 1 to 26. Those of ordinary skill in the art will recognize that when the compounds of Formula I which contain the polyoxyalkylene alcohol of Formula IV are used in a composition, y will not have a fixed value but will instead be represented by a range of different values. As used in this specification, y is considered to be a (number) average of the various values of y that are found in a given composition, which number has been rounded to the nearest integer. The range of y was determined by gel permeation chromatography (GPC) analysis in the various examples and is indicated in the various examples by the polydispersity (polydispersity= molecular weight based on the weight average divided by the molecular weight based on the number average).

When y is greater than 1, the individual $R_{11}$'s are the same or different. For example, if y is 20, each $R_{11}$ can be alkyl of four carbon atoms. Alternatively, the $R_{11}$'s can differ and for instance, independently be alkyl from two to four carbon atoms. When the $R_{11}$'s differ, they may be present in blocks, i.e., all y groups in which $R_{11}$ is alkyl of three carbon atoms will be adjacent, followed by all y groups in which $R_{11}$ is alkyl of two carbon atoms, followed by all y groups in which $R_{11}$ is alkyl of four carbon atoms. When the $R_{11}$'s differ, they may also be present in any random distribution.

In an alternative preferred embodiment of the present invention, $R_1$ will be polyoxyalkylene alcohol of Formula IV as defined hereinbefore. When $R_1$ is polyoxyalkylene alcohol of Formula IV, preferably the sum of the values of x and y will not exceed 40, more preferably the sum of the values of x and y will not exceed 26. In the most preferred embodiment of when $R_1$ is polyoxyalkylene alcohol of Formula IV, x will be from 1 to 13 and y will be from 1 to 13.

$R_2$ and $R_3$ are each independently selected from the group consisting of hydrogen, hydrocarbyl, as defined hereinbefore, of 1 to 100 carbon atoms and substituted hydrocarbyl, as defined hereinbefore, of 1 to 100 carbon atoms or $R_2$ and $R_3$ taken together with the carbon atom to which they are connected form a cyclic group of 4 to 100 carbon atoms. When $R_2$ and/or $R_3$ are hydrocarbyl or substituted hydrocarbyl, each $R_2$ and/or $R_3$ are preferably independently selected from hydrocarbyl of 1 to 50 carbon atoms and substituted hydrocarbyl of 1 to 50 carbon atoms. More preferably, $R_2$ and/or $R_3$ are independently selected from hydrocarbyl of 1 to 20 carbon atoms. Preferably $R_2$ and/or $R_3$ are each independently selected from hydrocarbyl comprising alkyl of 1 to 20 carbon atoms, cyclic alkyl of 4 to 20 carbon atoms and aromatic of 6 to 20 carbon atoms, more preferably alkyl of 1 to 10 carbon atoms, cyclic alkyl of 5 to 10 carbon atoms and aromatic of 6 to 10 carbon atoms and most preferably alkyl of 1 to 5 carbon atoms, cyclic alkyl of 5 to 8 carbon atoms and aromatic of 6 carbon atoms. In the most preferred embodiments, when $R_2$ and/or $R_3$ are hydrocarbyl, each is selected from alkyl of 1 to 20 carbon atoms and more preferably alkyl of 1 to 10 carbon atoms, most preferably methyl. $R_2$ and $R_3$ may be the same or different. In the most preferred embodiments, $R_2$ and $R_3$ will be the same.

When $R_2$ and/or $R_3$ are hydrocarbyl of a relatively high number of carbon atoms, i.e., greater than about 50 carbon atoms, $R_2$ and/or $R_3$ will be represented by polymeric hydrocarbyls derived from polyisobutylene, polybutene, polypropylene or poly-alphaolefin.

$R_2$ and $R_3$ can also be taken together with the carbon atom to which they are attached to form a cyclic group of 4 to 100 carbon atoms. As used herein, the term "cyclic group" refers to when $R_2$ and $R_3$ together with the carbon atom to which they are connected form an alicyclic ring or an arene. Note that for purposes of calculating the number of carbon atoms in the cyclic group when $R_2$ and $R_3$ are taken together to form a cyclic group, the carbon atom to which $R_2$ and $R_3$ are connected is included. Preferably when $R_2$ and $R_3$ are taken together with the carbon atom to which they are connected, they form a cyclic group of 5 to 50 carbon atoms, even more preferably of 5 to 20 carbon atoms and most preferably 5 to 8 carbon atoms.

As noted, when $R_2$ and $R_3$ taken together with the carbon atom to which they are connected form a "cyclic group", they will be a partial structure in the form of a ring which is alicyclic or arene. When $R_2$ and $R_3$ taken together form an alicyclic ring, the ring can be cycloalkyl or cycloalkenyl (i.e., cyclohexyl, cyclopentyl, cyclododecyl, cyclooctyl, cyclohexenyl or cyclopentenyl). In addition, the ring may be bicyclic (i.e., bicycloalkyl or bicycloalkenyl) or fused to additional ring structures to form polycyclic or multiple ring groups (i.e., norbonyl or bicyclo(3,3,1)nonyl). A variety of substituents such as one or more alkyl or aryl groups may also be present on any one or more of the rings (i.e., 2-methylcyclopentyl or 4-butylcyclohexyl). When substituents are present, they can be in a variety of forms, including but not limited to straight or branched chained alkyls. In addition, $R_2$ and $R_3$ can be taken together with the carbon atom to which they are connected to form an arene such as 9-fluorenyl. $R_2$ and $R_3$ can also be taken together with the carbon atom to which they are connected to form a "substituted cyclic group" which refers to any "cyclic group" which has a substituent attached to the cyclic group and the substituent includes a functional group such as carbonyl, carboxyl, nitro, amino, hydroxy, oxy, cyano, sulfonyl or sulfoxyl.

When $R_2$ and $R_3$ together form a cyclic group, they will preferably form a cycloalkyl or a bicycloalkyl of 5 to 50 carbon atoms, with cyclohexyl being the most preferred cycloalkyl and benzene derivatives and naphthalene derivatives being the most preferred bicycloalkyls.

Representative examples of $R_2$ and $R_3$ taken together to form cyclic groups are illustrated by the following partial structures: cycloalkyls such as cyclopentyl, cyclohexyl, cycloheptyl, cyclooctyl; substituted cycloalkyls such as methylcyclohexyl, ethylcyclohexyl, and butylcyclohexyl; bicycloalkyls such as bicyclo[2,2,1]heptyl, bicyclo [2,2,2] octyl and bicyclo[4,2,2]decyl; substituted bicycloalkyls such as methyl-bicyclo[2,2,1]heptyl and methyl-bicyclo[2,2,21] octyl; multiple rings such as benzocyclohexyl and benzocyclopentyl; substituted multiple rings which are derivatives from the Diels-Alder of dicyclopentadiene; and arenes such as 9-fluoroenyl.

Each $R_4$ is independently selected from the group consisting of hydrocarbyl, as defined hereinbefore, of 2 to 100 carbon atoms, or substituted hydrocarbyl, as defined hereinbefore, of 2 to 100 carbon atoms. Preferably each $R_4$ is independently hydrocarbyl or substituted hydrocarbyl of 2 to 50 carbon atoms, more preferably of 2 to 20 carbon atoms. The most preferred compounds are those in which each $R_4$ is independently selected from hydrocarbyl of 2 to 4 carbon atoms. When $R_4$ is hydrocarbyl of a relatively high number of carbon atoms, i.e., greater than about 50 carbon atoms, $R_4$ will be represented by polymeric hydrocarbyls derived from polyisobutylene, polybutene, polypropylene or poly-alphaolefins.

Particularly preferred compounds of Formula I are those in which $R_4$ is hydrocarbyl (geminal or vicinal) of Formula VII or Formula VIII:

(VII)

or

(VIII)

wherein $R_{15}$, $R_{16}$ and $R_{17}$ are each independently selected from hydrogen, hydrocarbyl, as defined hereinbefore, of 1 to 98 carbon atoms and substituted hydrocarbyl, as defined hereinbefore, of 1 to 98 carbon atoms. Preferably $R_{15}$, $R_{16}$ and $R_{17}$ are each independently selected from hydrogen, hydrocarbyl of 1 to 18 carbon atoms and substituted hydrocarbyl of 1 to 18 carbon atoms. $R_{16}$ and $R_{15}$, or in the alternative $R_{15}$ and $R_{17}$, may be taken together to form a divalent linking hydrocarbyl group of 3 to 12 carbon atoms.

The most preferred compounds of Formula I are those in which $R_4$ is hydrocarbyl as represented by Formula VII above wherein each $R_{17}$ is hydrogen and each $R_{15}$ is independently selected from hydrogen, alkyl of 1 to 18 carbon atoms and oxysubstituted hydrocarbyl of 1 to 18 carbon atoms, particularly those compounds where each $R_{17}$ is hydrogen and each $R_{15}$ is independently selected from hydrogen and alkyl of 1 to 2 carbon atoms, especially those compounds where each $R_{17}$ is hydrogen and each $R_{15}$ is alkyl of two carbon atoms.

When $R_{15}$ is oxy-substituted hydrocarbyl of 1 to 18 carbon atoms, $R_{15}$ is preferably an alkoxy-substituted alkylene of 1 to 18 carbon atoms or an aryloxy-substituted alkylene of 1 to 18 carbon atoms. Particularly preferred alkoxy-substituted alkylene groups include ethylhexyleneoxymethylene, isopropoxymethylene, butoxymethylene and mixtures thereof. Particularly preferred aryl-substituted alkylene groups include nonylphenoxymethylene, phenoxymethylene and mixtures thereof.

In Formula I above, x is from 1 to 50, preferably from 1 to 40, and even more preferably from 1 to 26. Those of ordinary skill in the art will recognize that when the compounds of Formula I are used in a composition, x will not have a fixed value but will instead be represented by a range of different values. As used in this specification, x is considered to be a (number) average of the various values of x that are found in a given composition, which number has been rounded to the nearest integer. The range of x was determined by gel permeation chromatography (GPC) analysis in the various examples and is indicated in the various examples by the polydispersity (polydispersity= molecular weight based on the weight average divided by the molecular weight based on the number average). The same is applicable with regard to y of Formula IV.

When x is greater than 1, the individual $R_4$'s are the same or different. For example, if x is 20, each $R_4$ can be alkyl of four carbon atoms. Alternatively, the $R_4$'s can differ and for instance, independently be alkyl from two to four carbon atoms. When the $R_4$'s differ, they may be present in blocks, i.e., all x groups in which $R_4$ is alkyl of three carbon atoms will be adjacent, followed by all x groups in which $R_4$ is alkyl of two carbon atoms, followed by all x groups in which $R_4$ is alkyl of four carbon atoms. When the $R_4$'s differ, they may also be present in any random distribution.

In one preferred embodiment of the present invention, $R_1$ is selected from hydrocarbyl of 1 to 100 carbon atoms, preferably alkyl of 1 to 20 carbon atoms and even more preferably methyl. In the preferred embodiment when $R_1$ is selected from hydrocarbyl of 1 to 100 carbon atoms, x will preferably range from 8 to 26.

The present invention is also directed to compounds of Formula I wherein $R_1$, $R_2$, $R_3$, $R_4$ and x are as defined hereinbefore.

The compounds of Formula I have a weight average molecular weight of at least 600. Preferably, the weight average molecular weight is from about 800 to about 4000, even more preferably from about 800 to about 2000.

Typical compounds represented by Formula I and the corresponding initiators used to make these compounds include those listed by structure in Table I.

TABLE I

| Initiator | Product |
|---|---|
| (structure shown) | (structure shown) wherein x is from 1 to 26 and y is from 1 to 26. |
| (structure shown) | (structure shown) wherein x is from 8 to 26. |

Additional non-limiting illustrative embodiments of the compounds useful as additives in the instant invention also include those of Formula II:

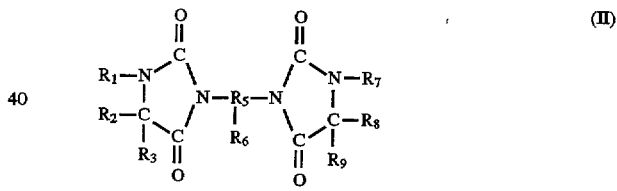

(II)

In Formula II, $R_1$ and $R_7$ are each independently selected from the group consisting of hydrocarbyl, as defined hereinbefore, of 1 to 100 carbon atoms, substituted hydrocarbyl, as defined hereinbefore, of 1 to 100 carbon atoms and polyoxyalkylene alcohol of 2 to 200 carbon atoms. $R_1$ and $R_7$ may be the same or different. In the most preferred embodiments, $R_1$ and $R_7$ are the same.

When $R_1$ and/or $R_7$ are hydrocarbyl or substituted hydrocarbyl, $R_1$ and/or $R_7$ are preferably selected from hydrocarbyl of 1 to 50 carbon atoms or substituted hydrocarbyl of 1 to 50 carbon atoms. Preferably, $R_1$ and/or $R_7$ are hydrocarbyl. Preferably when $R_1$ and/or $R_7$ are hydrocarbyl, they are hydrocarbyl independently selected from alkyl of 1 to 20 carbon atoms, cyclic alkyl of 4 to 20 carbon atoms and aromatic of 6 to 20 carbon atoms, more preferably alkyl of 1 to 10 carbon atoms, cyclic alkyl of 5 to 10 carbon atoms and aromatic of 6 to 10 carbon atoms and most preferably alkyl of 1 to 5 carbon atoms, cyclic alkyl of 5 to 8 carbon atoms and aromatic of 6 carbon atoms. In the more preferred embodiments, $R_1$ and/or $R_7$ are each independently hydrocarbyl selected from alkyl of 1 to 20 carbon atoms, more preferably alkyl of 1 to 10 carbon atoms and most preferably alkyl of 1 to 5 carbon atoms.

When $R_1$ and/or $R_7$ are hydrocarbyl of a relatively high number of carbon atoms, i.e., greater than about 50 carbon atoms, $R_1$ and/or $R_7$ will be polymeric hydrocarbyls derived from polyisobutylene, polybutene, polypropylene or poly-alphaolefin.

$R_6$ is selected from the group consisting of hydrogen, hydrocarbyl, as defined hereinbefore, of 1 to 100 carbon atoms, substituted hydrocarbyl, as defined hereinbefore, of 1 to 100 carbon atoms and polyoxyalkyl of Formula III:

wherein $R_{10}$ is selected from the group consisting of hydrocarbyl, as defined hereinbefore, of 1 to 100 carbon atoms, substituted hydrocarbyl, as defined hereinbefore, of 1 to 100 carbon atoms and polyoxyalkylene alcohol of 2 to 200 carbon atoms with the proviso that when both $R_1$ and $R_7$ are not polyoxyalkylene alcohol, $R_6$ must be polyoxyalkyl of Formula III wherein —$R_{10}$ is polyoxyalkylene alcohol of 2 to 200 carbon atoms.

When $R_6$ is hydrocarbyl or substituted hydrocarbyl, $R_6$ is preferably selected from hydrocarbyl of 1 to 50 carbon atoms or substituted hydrocarbyl of 1 to 50 carbon atoms. More preferably, $R_6$ is hydrocarbyl of 1 to 20 carbon atoms. When $R_6$ is hydrocarbyl, it is preferably hydrocarbyl comprising alkyl of 1 to 20 carbon atoms, cyclic alkyl of 4 to 20 carbon atoms and aromatic of 6 to 20 carbon atoms, more preferably alkyl of 1 to 10 carbon atoms, cyclic alkyl of 5 to 10 carbon atoms and aromatic of 6 to 10 carbon atoms, and most preferably alkyl of 1 to 5 carbon atoms, cyclic alkyl of 5 to 8 carbon atoms and aromatic of 6 carbon atoms. In the more preferred embodiments, when $R_6$ is hydrocarbyl, it is selected from alkyl of 1 to 20 carbon atoms, more preferably alkyl of 1 to 10 carbon atoms, and most preferably alkyl of 1 to 5 carbon atoms.

When $R_6$ is hydrocarbyl of a relatively high number of carbon atoms, i.e., greater than about 50 carbon atoms, $R_6$ will be represented by polymeric hydrocarbyls derived from polyisobutylene, polybutene, polypropylene or poly-alphaolefin.

$R_6$ can also be polyoxyalkyl. When $R_6$ is polyoxyalkyl, it will be polyoxyalkyl of Formula III:

wherein $R_{10}$ is selected from the group consisting of hydrocarbyl, as defined hereinbefore, of 1 to 100 carbon atoms, substituted hydrocarbyl, as defined hereinbefore, of 1 to 100 carbon atoms and polyoxyalkylene alcohol of 2 to 200 carbon atoms. When $R_{10}$ is hydrocarbyl or substituted hydrocarbyl, $R_{10}$ is preferably hydrocarbyl of 1 to 50 carbon atoms or substituted hydrocarbyl of 1 to 50 carbon atoms. More preferably, $R_{10}$ is hydrocarbyl of 1 to 20 carbon atoms, even more preferably, alkyl of 1 to 20 carbon atoms, and most preferably alkyl of 1 to 10 carbon atoms.

When $R_1$, $R_7$ and/or $R_{10}$ are polyoxyalkylene alcohol of 2 to 200 carbon atoms, $R_1$, $R_7$ and/or $R_{10}$ are preferably each polyoxyalkylene alcohol of Formula IX:

wherein each $R_{18}$ is independently selected from the group consisting of hydrocarbyl, as defined hereinbefore, of 2 to 100 carbon atoms and substituted hydrocarbyl, as defined hereinbefore, of 2 to 100 carbon atoms and z is from 1 to 50. Preferably, each $R_{18}$ is independently selected from hydrocarbyl of 2 to 100 carbon atoms. When $R_{18}$ is hydrocarbyl of a relatively high number of carbon atoms, i.e., greater than about 50 carbon atoms, each will be represented by polymeric hydrocarbyls derived from polyisobutylene, polybutene, polypropylene or poly-alphaolefin. More preferably, each $R_{18}$ is independently selected from hydrocarbyl of 2 to 20 carbon atoms. Particularly preferred compounds are those in which each $R_{18}$ is independently alkyl of 2 to 20 carbon atoms, more preferably alkyl of 2 to 4 carbon atoms, especially alkyl of 4 carbon atoms.

Particularly preferred compounds of Formula II are those in which when $R_1$, $R_7$ and/or $R_{10}$ are polyoxyalkylene alcohol of Formula IX, $R_{18}$ is hydrocarbyl (geminal or vicinal) of Formula X or Formula XI:

or

wherein $R_{19}$, $R_{20}$ and $R_{21}$, are each independently selected from hydrogen, hydrocarbyl, as defined hereinbefore, of 1 to 98 carbon atoms and substituted hydrocarbyl, as defined hereinbefore, of 1 to 98 carbon atoms. Preferably $R_{19}$, $R_{20}$ and $R_{21}$ are each independently selected from hydrogen, hydrocarbyl of 1 to 18 carbon atoms and substituted hydrocarbyl of 1 to 18 carbon atoms. $R_{19}$ and $R_{20}$, or in the alternative $R_{19}$ and $R_{21}$, may be taken together to form a divalent linking hydrocarbyl group of 3 to 12 carbon atoms.

The most preferred compounds of Formula II are those in which when $R_1$, $R_7$ and/or $R_{10}$ are polyoxyalkylene alcohol, $R_{18}$ is hydrocarbyl as represented by Formula X above wherein each $R_{21}$ is hydrogen and each $R_{19}$ is independently selected from hydrogen, alkyl of 1 to 18 carbon atoms and oxy-substituted hydrocarbyl of 1 to 18 carbon atoms, particularly those compounds where each $R_{21}$ is hydrogen and each $R_{19}$ is independently selected from hydrogen and alkyl of 1 to 2 carbon atoms, especially those compounds where each $R_{21}$ is hydrogen and each $R_{19}$ is alkyl of two carbon atoms.

When $R_{19}$ is oxy-substituted hydrocarbyl of 1 to 18 carbon atoms, $R_{19}$ is preferably an alkoxy-substituted alkylene of 1 to 18 carbon atoms or an aryloxy-substituted alkylene of 1 to 18 carbon atoms. Particularly preferred alkoxy-substituted alkylene groups include ethylhexyleneoxymethylene, isopropoxymethylene, butoxymethylene and mixtures thereof. Particularly preferred aryl-substituted alkylene groups include nonylphenoxymethylene, phenoxymethylene and mixtures thereof.

In Formula IX above, z is from 1 to 50, preferably from 1 to 40, and even more preferably from 1 to 26. When two or more polyoxyalkylene alcohol groups of the Formula IX are present, z will preferably be from 1 to 13. Those of ordinary skill in the art will recognize that when compounds of Formula I which contain the polyoxyalkylene alcohol of Formula IX are used in a composition, z will not have a fixed value but will instead be represented by a range of different values. As used in this specification, z is considered to be a (number) average of the various values of z that are found in a given composition, which number has been rounded to the nearest integer. The range of z was determined by gel permeation chromatography (GPC) analysis in the various examples and is indicated in the various examples by the polydispersity (polydispersity=molecular weight based on the weight average divided by the molecular weight based on the number average).

When z is greater than 1, the individual $R_{18}$'s are the same or different. For example, if z is 20, each $R_{18}$ can be alkyl of four carbon atoms. Alternatively, the $R_{18}$'s can differ and for instance, independently be alkyl from two to four carbon atoms. When the $R_{18}$'s differ, they may be present in blocks, i.e., all z groups in which $R_{18}$ is alkyl of three carbon atoms will be adjacent, followed by all z groups in which $R_{18}$ is alkyl of two carbon atoms, followed by all z groups in which $R_{18}$ is alkyl of four carbon atoms. When the $R_{18}$'s differ, they may also be present in any random distribution.

As previously noted, when $R_1$ and $R_7$ are not polyoxyalkylene alcohol, $R_6$ must be polyoxyalkyl of Formula III (—O—$R_{10}$) and $R_{10}$ must be polyoxyalkylene alcohol of 2 to 200 carbon atoms. In one embodiment, when $R_1$ and $R_7$ are not polyoxyalkylene alcohol and $R_6$ is polyoxyalkyl of Formula II wherein $R_{10}$ is polyoxyalkylene alcohol of Formula IX, z will preferably range from 8 to 26. In another preferred embodiment, $R_1$ and $R_7$ are each polyoxyalkylene alcohol of 2 to 200 carbon atoms and $R_6$ is polyoxyalkyl of the formula —O—$R_{10}$ wherein $R_{10}$ is polyoxyalkylene alcohol of 2 to 200 carbon atoms. In the preferred embodiment when $R_1$ and $R_7$ are polyoxyalkylene alcohol of 2 to 200 carbon atoms and $R_6$ is polyoxyalkyl of the formula —O—$R_{10}$ wherein $R_{10}$ is polyoxyalkylene alcohol of 2 to 200 carbon atoms, the sum of the values of all three z's will preferably not exceed 40 and even more preferably the sum of the values of all three z's will not exceed 26. In a still alternative preferred embodiment, $R_1$ and $R_7$ are each independently polyoxyalkylene alcohol of 2 to 200 carbon atoms and $R_6$ is hydrogen or alkyl of 1 to 10 carbon atoms. In the preferred embodiment when $R_1$ and $R_7$ are each independently polyoxyalkylene alcohol of 2 to 200 carbon atoms and $R_6$ is hydrogen or alkyl of 1 to 10 carbon atoms, the sum of the values of both z's will preferably not exceed 40, even more preferably, the sum of the values of both z's will not exceed 26.

$R_5$ is selected from the group consisting of hydrocarbyl, as defined hereinbefore, of 1 to 100 carbon atoms and substituted hydrocarbyl, as defined hereinbefore, of 1 to 100 carbon atoms. Preferably, $R_5$ is hydrocarbyl or substituted hydrocarbyl of 1 to 50 carbon atoms and even more preferably of 1 to 20 carbon atoms. In the more preferred embodiments, $R_5$ is hydrocarbyl comprising alkylene of 1 to 20 carbon atoms, even more preferably alkylene of 1 to 10 carbon atoms and most preferably alkylene of 1 to 3 carbon atoms.

$R_2$, $R_3$, $R_8$ and $R_9$ are each independently selected from the group consisting of hydrogen, hydrocarbyl, as defined hereinbefore, of 1 to 100 carbon atoms and substituted hydrocarbyl, as defined hereinbefore, of 1 to 100 carbon atoms. In the alternative, $R_2$ and $R_3$ taken together with the carbon atom to which they are connected form a cyclic group of 4 to 100 carbon atoms or $R_8$ and $R_9$ taken together with the carbon atom to which they are connected form a cyclic group of 4 to 100 carbon atoms. In one embodiment, $R_2$ and $R_3$ taken together form a cyclic group of 4 to 100 carbon atoms and $R_8$ and $R_9$ taken together form a cyclic group of 4 to 100 carbon atoms. In an additional embodiment, only one of the two groups ($R_2$ and $R_3$ or $R_8$ and $R_9$) form a cyclic group of 4 to 100 carbon atoms.

When $R_2$, $R_3$, $R_8$ and/or $R_9$ are hydrocarbyl or substituted hydrocarbyl, $R_2$, $R_3$, $R_8$ and/or $R_9$ are preferably each independently selected from hydrocarbyl of 1 to 50 carbon atoms or substituted hydrocarbyl of 1 to 50 carbon atoms. More preferably, $R_2$, $R_3$, $R_8$ and/or $R_9$ are each independently selected from hydrocarbyl of 1 to 20 carbon atoms. Preferably $R_2$, $R_3$, $R_8$ and/or $R_9$ are each independently selected from hydrocarbyl comprising alkyl of 1 to 20 carbon atoms, cyclic alkyl of 1 to 20 carbon atoms and aromatic of 1 to 20 carbon atoms. In the most preferred embodiments, when $R_2$, $R_3$, $R_8$ and/or $R_9$ are hydrocarbyl or substituted hydrocarbyl, each is independently selected from alkyl of 1 to 20 carbon atoms, more preferably alkyl of 1 to 10 carbon atoms and most preferably alkyl of 1 carbon atom. $R_2$, $R_3$, $R_8$ and $R_9$ may be the same or different. In the most preferred embodiments, they are all the same.

When $R_2$, $R_3$, $R_8$ and/or $R_9$ are hydrocarbyl of a relatively high number of carbon atoms, i.e., greater than about 50 carbon atoms, $R_2$, $R_3$, $R_8$ and/or $R_9$ will each independently be represented by polymeric hydrocarbyls derived from polyisobutylene, polybutene, polypropylene or polyalphaolefins.

As noted, $R_2$ and $R_3$ taken together with the carbon atom to which they are connected can form a cyclic group of 4 to 100 carbon atoms. In addition, $R_8$ and $R_9$ taken together with the carbon atom to which they are connected can form a cyclic group of 4 to 100 carbon atoms. As used herein, the term "cyclic group" refers to when $R_2$ and $R_3$ and/or $R_8$ and $R_9$ are taken together with the carbon atom to which they are connected to form an alicyclic ring or an arene. Note that for purposes of calculating the number of carbon atoms in the cyclic group when $R_2$ and $R_3$ are taken together to form a cyclic group the carbon atom to which they are connected is included. The same applies with regard to when $R_8$ and $R_9$ are taken together to form a cyclic group. Preferably when $R_2$ and $R_3$ and/or $R_8$ and $R_9$ are taken together, they form a cyclic group of 5 to 50 carbon atoms, even more preferably of 5 to 20 carbon atoms and most preferably 5 to 8 carbon atoms.

As noted, when $R_2$ and $R_3$ and/or $R_8$ and $R_9$ taken together form a "cyclic group", they will be a partial structure in the form of a ring which will be alicyclic or arene. When $R_2$ and $R_3$ and/or $R_8$ and $R_9$ taken together form an alicyclic ring, the ring can be cycloalkyl or cycloalkenyl (i.e., cyclohexyl, cyclopentyl, cyclododecyl, cyclooctyl, cyclohexenyl or cyclopentyl). In addition, the ring may be bicyclic (i.e., bicycloalkyl or bicycloalkenyl) or fused to additional ring structures to form polycyclic or multiple ring groups (i.e., norbonyl or bicyclo(3,3,1)nonyl). A variety of substituents such as one or more alkyl groups or aryl groups may also be present on any one or more of the rings (i.e., 2-methylcyclopentyl or 4-butylcyclohexyl). When substituents are present, they can be in a variety of forms, including but not limited to straight or branched chained alkyls. In addition, $R_2$ and $R_3$ and/or $R_8$ and $R_9$ can be taken together with the carbon atom to which they are connected to form an arene such as 9-fluorenyl. $R_2$ and $R_3$ and/or $R_8$ and $R_9$ can also be taken together to form a "substituted cyclic group" which refers to any "cyclic group" which has a substituent attached to the cyclic group and the substituent includes a functional group such as carbonyl, carboxyl, nitro, amino, hydroxy, oxy, cyano, sulfonyl or sulfoxyl.

When $R_2$ and $R_3$ and/or $R_8$ and $R_9$ together form a cyclic group, they will preferably form a cycloalkyl or a bicycloalkyl of 5 to 20 carbon atoms, with cyclohexyl being the most preferred cycloalkyl and benzene derivatives and naphthalene derivatives being the most preferred bicycloalkyls.

Representative examples of $R_2$ and $R_3$ and/or $R_8$ and $R_9$ taken together to form cyclic groups are illustrated by the following partial structures: cycloalkyls such as cyclopentyl, cyclohexyl, cycloheptyl, cyclooctyl; substituted cycloalkyls such as methylcyclohexyl, ethylcyclohexyl, and butylcyclohexyl; bicycloalkyls such as bicyclo[2,2,1]heptyl, bicyclo

[2,2,21]octyl and bicyclo[4,2,2]decyl; substituted bicycloalkyls such as methyl-bicyclo[2,2,1]heptyl and methyl-bicyclo[2,2,2]octyl; multiple rings such as benzocyclohexyl and benzocyclopentyl; substituted multiple rings which are derivatives from the Diels-Alder of dicyclopentadiene; and arenes such as 9-fluorenyl.

Typical compounds represented by Formula II and the corresponding initiators used to make these compounds include those listed by structure in Table 2.

TABLE 2

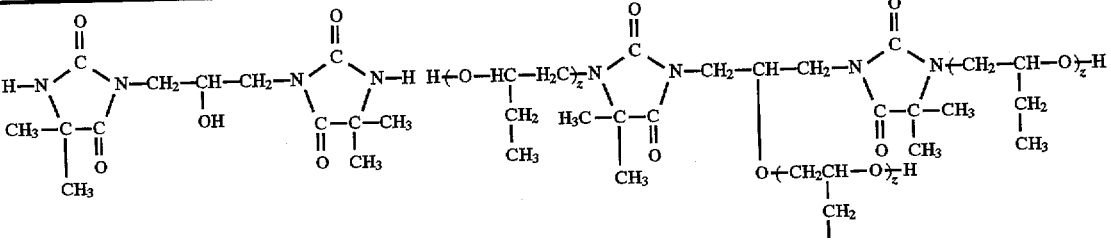

wherein each z is from 1 to 26.

The compounds of Formula II each have a weight average molecular weight of at least 600. Preferably, the weight average molecular weight is from about 800 to about 4000, even more preferably from about 800 to about 2000.

PREPARATION OF COMPOUNDS

The compounds of Formula I are illustratively prepared by alkoxylation, i.e., reacting an initiator selected from hydantoin and hydantoin alcohols with one or more epoxides in the presence of a potassium compound.

In one embodiment, the compounds of Formula I are prepared utilizing epoxides and hydantoin initiators represented by Formula XII:

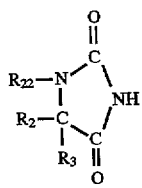

(XII)

wherein $R_2$ and $R_3$ are as defined hereinbefore and $R_{22}$ is selected from the group consisting of hydrogen, hydrocarbyl, as defined hereinbefore, of 1 to 100 carbon atoms and substituted hydrocarbyl, as defined hereinbefore, of 1 to 100 carbon atoms. Non-limiting examples of hydantoin initiators which are employed to prepare the compounds of the present invention include: 4-methylhydantoin, 5,5'-dimethylhydantoin, 5-methyl-5-ethylhydantoin and 5-phenylhydantoin, with 5,5'-dimethylhydantoin being the most preferred. Select hydantoin initiators of Formula XII are also available commercially, such as, Hydantoin (available commercially from Chemical Dynamics Corp. and also available commercially from Penta Manufacturing Company) and 5,5'-dimethyl-hydantoin (available commercially from Chemical Dynamics Corp.).

The hydantoin initiators utilized can also be prepared using any of the methods known and described in the art, for example in U.S. Pat. No. 4,209,608, incorporated herein by reference. In U.S. Pat. No. 4,209,608 hydantoin initiators such as those represented by Formula XII in which $R_{22}$ is hydrogen are formed by reacting a given ketone or aldehyde, sodium cyanide and ammonium carbonate. Those of ordinary skill in the art will recognize that known procedures may be used to substitute hydrocarbyls or substituted hydrocarbyls for the hydrogen of $R_{22}$.

In an alternative embodiment, the compounds of Formula I are prepared utilizing epoxides and hydantoin alcohol initiators represented by general Formula XIII:

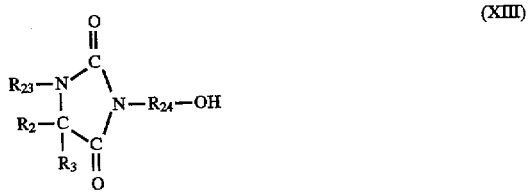

(XIII)

wherein $R_2$ and $R_3$ are as defined hereinbefore, $R_{23}$ is selected from the group consisting of hydrogen, hydrocarbyl of 1 to 100 carbon atoms and substituted hydrocarbyl of 1 to 100 carbon atoms and $R_{24}$ is selected from hydrocarbyl of 2 to 100 carbon atoms and substituted hydrocarbyl of 2 to 100 carbon atoms. Non-limiting examples of hydantoin alcohol initiators which can be employed include 5,5-dimethyl-hydantoin(2)-ethanol, 4-methyl-hydantoin(2)-ethanol and 5-methyl-5-ethylhydantoin (2)-ethanol, with 5,5-dimethyl-hydantoin(2)-ethanol being the most preferred.

The hydantoin alcohol initiators utilized can also be prepared by any of the methods known and described in the art, for example in U.S. Pat. No. 3,907,719, incorporated herein by reference.

The compounds of Formula II are illustratively prepared by alkoxylation, i.e., reacting an initiator selected from bis-hydantoins and hydantoin alcohols with one or more epoxides in the presence of a potassium compound.

In one embodiment, the compounds of Formula II are prepared utilizing epoxides and bis-hydantoin initiators represented by Formula XIV:

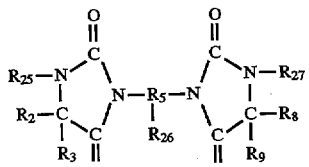

(XIV)

wherein $R_2$, $R_3$, $R_5$, $R_8$ and $R_9$ are as defined hereinbefore. $R_{25}$, $R_{26}$ and $R_{27}$ are each independently selected from hydrogen, hydrocarbyl, as defined hereinbefore, of 1 to 100 carbon atoms and substituted hydrocarbyl, as defined hereinbefore, of 1 to 100 carbon atoms with the proviso that when $R_{22}$ and $R_{27}$ are hydrocarbyl or substituted hydrocarbyl, $R_{26}$ must be hydrogen. Non-limiting examples of bis-hydantoin initiators which are employedinclude 1,1'-methylenebis-(5-ethyl-5-methyl)-hydantoin, 1,1-methylene-bis(5,5-dimethyl)-hydantoin, 1,2-ethylene-bis(5,5-dimethyl)-hydantoin and 1,1'-propylene-bis-(5-ethyl-5-methyl)-hydantoin, 1,1-propylene-bis(5,5-dimethyl)-hydantoin.

The bis-hydantoin initiators utilized can also be prepared by any of the methods known and described in the art, for example in U.S. Pat. No. 4,209,608, incorporated herein by reference. For example, in U.S. Pat. No. 4,209,608, bis-hydantoin initiators are formed by reacting a given ketone or aldehyde, sodium cyanide and ammonium carbonate to form an intermediate hydantoin of Formula XV or Formula XVI:

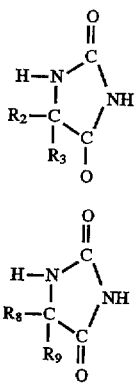

(XV)

(XVI)

wherein $R_2$, $R_3$, $R_8$ and $R_9$ are as defined hereinbefore. Two moles of the intermediate hydantoins (one mole each) is then condensed with formaldehyde under acidic conditions in the presence of a metal halide catalyst if necessary to produce a bis-hydantoin initiator wherein $R_5$ is a methylene. Those of ordinary skill in the art will recognize that known procedures may be used to substitute hydrocarbyls or substituted hydrocarbyls for the hydrogens in positions $R_{25}$ and $R_{27}$.

Bis-hydantoins of Formula XIV wherein $R_5$ is an alkylene group which contains more than one carbon atom may be prepared by condensing two moles of the intermediate hydantoin of Formulas XV and XVI with a bis-acetal of Formula XVII:

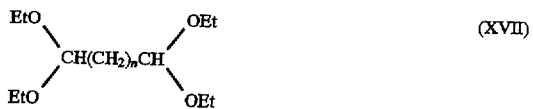

(XVII)

wherein n is 1 to 5, under anhydrous conditions followed by hydrogenation of the unsaturated intermediate.

In an alternative embodiment, the compounds of Formula II are prepared utilizing epoxides and hydantoin alcohol initiators represented by the general formula:

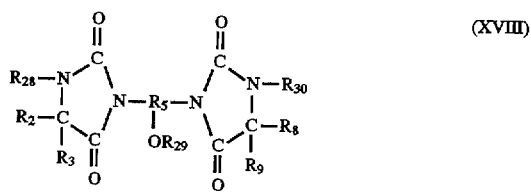

(XVIII)

wherein $R_2$, $R_3$, $R_5$, $R_8$ and $R_9$ are as defined hereinbefore, $R_{28}$ and $R_{30}$ are selected from the group consisting of hydrogen, hydrocarbyl, as defined hereinbefore, of 1 to 100 carbon atoms and substituted hydrocarbyl, as defined hereinbefore, of 1 to 100 carbon atoms and $R_{29}$ is selected from the group consisting of hydrogen and hydroxyalkyl of the formula:

(XIX)

wherein $R_{31}$ is selected from the group consisting of alkyl of 1 to 20 carbon atoms. Non-limiting examples of hydantoin alcohol initiators which can be employed include 1,3-bis(5', 5'-dimethyl-hydantoinyl-3')-propan-2-ol, 1,3-bis (5,5'-pentamethylene-hydantoinyl-3')-propan-2-ol and 1,3-bis(5, 5'-tetramethylene-hydantoinyl-3)-propan-2-ol, with 1,3-bis (5,5'-dimethylhydantoinyl-3')-propan-2-ol being the most preferred.

The bis-hydantoin alcohol initiators utilized can also be prepared by any of the methods known and described in the art, for example in U.S. Pat. No. 3,907,719 and U.S. Pat. No. 3,821,243, each incorporated herein by reference. For example, in U.S. Pat. No. 3,907,719, an intermediate hydantoin of the formula:

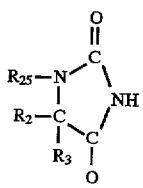

(XX)

or

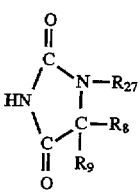

(XXI)

wherein $R_2$, $R_3$, $R_5$, $R_8$, $R_9$, $R_{25}$ and $R_{27}$ are as defined hereinbefore, is formed by reacting a given ketone, sodium cyanide and ammonium carbonate. Two moles of the intermediate hydantoin are then reacted with one mole of glycerin dichlorohydrin (1,3-dichloropropan-2-ol) in the presence of potassium carbonate and dimethylformamide to form the bis-hydantoin alcohol initiator of Formula XVIII.

The one or more epoxides employed in the reaction with the initiators to prepare the compounds of Formula I and Formula II contain from 2 to 100 carbon atoms, preferably from 2 to 50 carbon atoms, more preferably from 2 to 20 carbon atoms, even more preferably from 2 to 4 carbon atoms, and most preferably from 4 carbon atoms. The epoxides may be internal epoxides such as 2,3 epoxides of the formula:

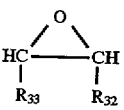

(XXII)

wherein $R_{32}$ and $R_{33}$ are selected from the group consisting of hydrogen, hydrocarbyl, as defined hereinbefore, of 1 to 98 carbon atoms and substituted hydrocarbyl, as defined hereinbefore, of 1 to 98 carbon atoms or terminal epoxides such as 1,2 epoxides of the formula:

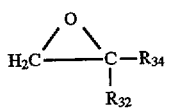

(XXIII)

wherein $R_{32}$ and $R_{34}$ are selected from the group consisting of hydrogen, hydrocarbyl, as defined hereinbefore, or 1 to 98 carbon atoms and substituted hydrocarbyl, as defined hereinbefore, of 1 to 98 carbon atoms. (Note that Formulas XXII and XXIII correspond to geminal and vicinal hydrocarbyls as represented by Formulas V and VI for $R_{11}$ in Formula I; Formulas VII and VIII for $R_4$ in Formula I; and Formulas X and XI for $R_1$, $R_7$ and $R_{10}$ in Formula II). In both Formulas XXII and XXIII, $R_{32}$ and $R_{33}$, or alternatively $R_{32}$ and $R_{34}$, may be taken together to form a cycloalkylene epoxide or a vinylidene epoxide by forming a divalent linking hydrocarbyl group of 3 to 12 carbon atoms.

When $R_{32}$, $R_{33}$ and/or $R_{34}$ are oxy-substituted hydrocarbyl, suitable compounds of Formulas XXII and XXIII will include compounds such as nonylphenyl glycidyl ether, phenyl glycidyl ether, cresyl glycidyl ether, butyl glycidyl ether, alkyl $C_{12}$–$C_{13}$ glycidyl ether, alkyl $C_8$–$C_{10}$ glycidyl ether, 2-ethylhexyl glycidyl ether and isopropyl glycidyl ether.

In the preferred embodiment, the terminal epoxides represented by Formula XXIII are utilized. Ideally these terminal epoxides are 1,2-epoxyalkanes. Suitable 1,2-epoxyalkanes include 1,2-epoxyethane, 1,2-epoxypropane, 1,2-epoxybutane, 1,2-epoxydecane, 1,2-epoxydodecane, 1,2-epoxyhexadecane, 1,2-epoxyoctadecane and mixtures thereof.

In a typical preparation of Formula I compounds and Formula II compounds, the one or more epoxides and initiator are contacted at a ratio from about 7:1 to about 55:1 moles of epoxide per mole of initiator. Preferably, they are contacted at a molar ratio from about 10:1 to about 30:1, with the most preferred molar ratio being about 20:1.

The reaction is carried out in the presence of potassium compounds which act as alkoxylation catalysts. Such catalysts are conventional and include potassium methoxide, potassium ethoxide, potassium hydroxide, potassium hydride and potassium-t-butoxide. The preferred catalysts are potassium hydroxide and potassium-t-butoxide. The catalysts are used in a base stable solvent such as alcohol, ether or hydrocarbons. The catalysts are employed in a wide variety of concentrations. Generally, the potassium compounds will be used in an amount from about 0.02% to about 5.0% of the total weight of the mixture, preferably from about 0.1% to about 2.0% of the total weight of the mixture, and most preferably about 0.2% of the total weight of the mixture.

The reaction is conveniently carried out in a conventional autoclave reactor equipped with heating and cooling means. The process is practiced batchwise, continuously or semi-continuously.

The manner in which the alkoxylation reaction is conducted is not critical to the invention. Illustratively, the initiator and potassium compound are mixed and heated under vacuum for a period of at least 30 minutes. The one or more epoxides are then added to the resulting mixture, the reactor sealed and pressurized with nitrogen, and the mixture stirred while the temperature is gradually increased.

The temperature for alkoxylation is from about 80° C. to about 250° C., preferably from about 100° C. to about 150° C., and even more preferably from about 120° C. to about 140° C. The alkoxylation reaction time is generally from about 2 to about 20 hours, although longer or shorter times are employed.

Alkoxylation processes of the above type are known and are described, for example in U.S. Pat. No. 4,973,414, U.S. Pat. No. 4,883,826, U.S. Pat. No. 5,123,932 and U.S. Pat. No. 4,612,335, each incorporated herein by reference.

The product of Formula I and Formula II is normally liquid and is recovered by conventional techniques such as filtration and distillation. The product is used in its crude state or is purified, if desired, by conventional techniques such as aqueous extraction, solid absorption and/or vacuum distillation to remove any remaining impurities.

Other methods for making the compounds of Formula I and Formula II are known by those skilled in the art. For example, the compounds of Formula I and Formula II are prepared by reacting an initiator as described hereinbefore with other cyclic ethers. In addition, other catalyst chemistry, such as the use of acidic catalysts, can be employed to achieve the compounds of Formula I and Formula II.

Fuel Compositions

The compounds of Formula I and Formula II are useful as additives in fuel compositions which are burned or combusted in internal combustion engines. The fuel compositions of the present invention comprise a major amount of a mixture of hydrocarbons in the gasoline boiling range and a minor amount of one or more of the compounds of Formula I, Formula II or mixtures thereof. As used herein, the term "minor amount" means less than about 10% by weight of the total fuel composition, preferably less than about 1% by weight of the total fuel composition and more preferably less than about 0.1% by weight of the total fuel composition.

Suitable liquid hydrocarbon fuels of the gasoline boiling range are mixtures of hydrocarbons having a boiling range of from about 25° C. to about 232° C. and comprise mixtures of saturated hydrocarbons, olefinic hydrocarbons and aromatic hydrocarbons. Preferred are gasoline mixtures having a saturated hydrocarbon content ranging from about 40% to about 80% by volume, an olefinic hydrocarbon content from 0% to about 30% by volume and an aromatic hydrocarbon content from about 10% to about 60% by volume. The base fuel is derived from straight run gasoline, polymer gasoline, natural gasoline, dimer and trimerized olefins, synthetically produced aromatic hydrocarbon mixtures, or from catalytically cracked or thermally cracked petroleum stocks, and mixtures of these. The hydrocarbon composition and octane level of the base fuel are not critical. The octane level, (R+M)/2, will generally be above about 85.

Any conventional motor fuel base can be employed in the practice of the present invention. For example, hydrocarbons in the gasoline can be replaced by up to a substantial amount of conventional alcohols or ethers, conventionally known for use in fuels. The base fuels are desirably substantially free of water since water could impede a smooth combustion.

Normally, the hydrocarbon fuel mixtures to which the invention is applied are substantially lead-free, but may contain minor amounts of blending agents such as methanol, ethanol, ethyl tertiary butyl ether, methyl tertiary butyl ether, and the like, at from about 0.1% by volume to about 15% by volume of the base fuel, although larger amounts may be utilized. The fuels can also contain conventional additives including antioxidants such as phenolics, e.g., 2,6-di-tert-butylphenol or phenylenediamines, e.g., N,N'-di-sec-butyl-p-phenylenediamine, dyes, metal deactivators, dehazers such as polyester-type ethoxylated alkylphenol-formaldehyde resins. Corrosion inhibitors, such as a polyhydric alcohol ester of a succinic acid derivative having on at least one of -its alpha-carbon atoms an unsubstituted or substituted aliphatic hydrocarbon group having from 20 to 500 carbon atoms, for example, pentaerythritol diester of polyisobutylene-substituted succinic acid, the polyisobutylene group having an average molecular weight of about 950, in an amount from about 1 ppm by weight to about 1000 ppm by weight, may also be present. The fuels can also contain antiknock compounds such as methyl cyclopentadienylmanganese tricarbonyl and ortho-azidophenol as well as co-antiknock compounds such as benzoyl acetone.

An effective amount of one or more compounds of Formula I and/or Formula II is introduced into the combustion zone of the engine in a variety of ways to prevent build-up of deposits, or to accomplish the reduction of intake valve deposits or the modification of existing deposits that are related to octane requirement. As mentioned, a preferred method is to add a minor amount of one or more compounds of Formula I and/or Formula II to the fuel. For example, one or more compounds of Formula I and/or Formula II are added directly to the fuel or are blended with one or more carriers and/or one or more additional detergents to form an additive concentrate. The additive concentrate can be added to the fuel at a later time.

The amount of hydantoin-containing polyether alcohol used will depend on the particular variation of Formula I and/or Formula II used, the engine, the fuel, and the presence or absence of carriers and additional detergents. Generally, each compound of Formula I and/or Formula II is added in an amount up to about 1000 ppm by weight, especially from about 1 ppm by weight to about 600 ppm by weight based on the total weight of the fuel composition. Preferably, the amount will be from about 50 ppm by weight to about 400 ppm by weight, and even more preferably from about 75 ppm by weight to about 250 ppm by weight based on the total weight of the fuel composition.

The carrier, when utilized, will have a weight average molecular weight from about 500 to about 5000. Suitable carriers, when utilized, include hydrocarbon based materials such as polyisobutylenes (PIB's), polypropylenes (PP's) and polyalphaolefins (PAO's); polyether based materials such as polybutylene oxides. (poly BO's), polypropylene oxides (poly PO's), polyhexadecene oxides (poly HO's) and mixtures thereof (i.e., both (poly BO)+(poly PO) and (poly-BO-PO)); and mineral oils such as Exxon Naphthenic 900 sus and high viscosity index (HVI) oils. The carrier is preferably selected from PIB's, poly BO's, and poly PO's, with poly BO's being the most preferred.

The carrier concentration in the final fuel composition is up to about 1000 ppm by weight. When a carrier is present, the preferred concentration is from about 50 ppm by weight to about 400 ppm by weight, based on the total weight of the fuel composition. Once the carrier is blended with one or more compounds of Formula I and/or Formula II, the blend is added directly to the fuel or packaged for future use.

The fuel compositions of the present invention may also contain one or more additional detergents. When additional detergents are utilized, the fuel composition will comprise a mixture of a major amount of hydrocarbons in the gasoline boiling range as described hereinbefore, a minor amount of one or more compounds of Formula I and/or Formula II as described hereinbefore and a minor amount of an additional detergent selected from polyalkylenyl amines, Mannich amines, polyalkenyl succinimides, poly(oxyalkylene) carbamates, poly(alkenyl)-N-substituted carbamates and mixtures thereof. As noted above, a carrier as described hereinbefore may also be included. As used herein, the term "minor amount" means less than about 10% by weight of the total fuel composition, preferably less than about 1% by weight of the total fuel composition and more preferably less than about 0.1% by weight of the total fuel composition.

The polyalkylenyl amine detergents utilized comprise at least one monovalent hydrocarbon group having at least 50 carbon atoms and at least one monovalent hydrocarbon group having at most five carbon atoms bound directly to separate nitrogen atoms of a diamine. Preferred polyalkylenyl amines are polyisobutenyl amines. Polyisobutenyl amines are known in the art and representative examples are disclosed in various U.S. Patents including U.S. Pat. No. 3,753,670, U.S. Pat. No. 3,756,793, U.S. Pat. No. 3,574,576 and U.S. Pat. No. 3,438,757, each incorporated herein by reference. Particularly preferred polyisobutenyl amines for use in the present fuel composition include N-polyisobutenyl-N',N'-dimethyl-1,3-diaminopropane (PIB-DAP) and OGA-472 (a polyisobutenyl ethylene diamine available commercially from Oronite).

The Mannich amine detergents utilized comprise a condensation product of a high molecular weight alkyl-substituted hydroxyaromatic compound, an amine which contains an amino group having at least one active hydrogen atom (preferably a polyamine), and an aldehyde. Such Mannich amines are known in the art and are disclosed in U.S. Pat. No. 4,231,759, incorporated herein by reference. Preferably, the Mannich amine is an alkyl substituted Mannich amine.

The polyalkenyl succinimide detergents comprise the reaction product of a dibasic acid anhydride with either a polyoxyalkylene diamine, a hydrocarbyl polyamine or mixtures of both. Typically the succinmide is substituted with the polyalkenyl group but the polyalkenyl group may be found on the polyoxyalkylene diamine or the hydrocarbyl polyamine. Polyalkenyl succinimides are also known in the art and representative examples are disclosed in various U.S. Patents including U.S. Pat. No. 4,810,261, U.S. Pat. No. 4,852,993, U.S. Pat. No. 4,968,321, U.S. Pat. No. 4,985,047, U.S. Pat. No. 5,061,291 and U.S. Pat. No. 5,147,414, each incorporated herein by reference.

The poly(oxyalkylene) carbamate detergents comprise an amine moiety and a poly(oxyalkylene) moiety linked together through a carbamate linkage, i.e.,

$$-O-C(O)-N- \quad (XXIV)$$

These poly(oxyalkylene) carbamates are known in the art and representative examples are disclosed in various U.S. Patents including, U.S. Pat. No. 4,191,537, U.S. Pat. No. 4,160,648, U.S. Pat. No. 4,236,020, U.S. Pat. No. 4,270,930, U.S. Pat. No. 4,288,612 and U.S. Pat. No. 4,881,945, each incorporated herein by reference. Particularly preferred poly (oxyalkylene) carbamates for use in the present fuel composition include OGA-480 (a poly(oxyalkylene) carbamate which is available commercially from Oronite).

The poly(alkenyl)-N-substituted carbamate detergents utilized are of the formula:

$$R-A-\overset{O}{\underset{\|}{C}}-OR^1 \quad (XXV)$$

in which R is a poly(alkenyl) chain; $R^1$ is a hydrocarbyl or substituted hydrocarbyl group; and A is an N-substituted amino group. Poly(alkenyl)-N-substituted carbamates are known in the art and are disclosed in U.S. Pat. No. 4,936,868, incorporated herein by reference.

The one or more additional detergents are added directly to the hydrocarbons, blended with one or more carriers, blended with one or more compounds of Formula I and/or Formula II, or blended with one or more compounds of Formula I and/or Formula II and one or more carriers before being added to the hydrocarbons.

The concentration of the one or more additional detergents in the final fuel composition is generally up to about 1000 ppm by weight for each additional detergent. When one or more additional detergents are utilized, the preferred concentration for each additional detergent is from about 50 ppm by weight to about 400 ppm by weight, based on the total weight of the fuel composition, even more preferably from about 75 ppm by weight to about 250 ppm by weight, based on the total weight of the fuel composition.

Engine Tests

Decreasing Intake Valve Deposits

The invention further provides a process for decreasing intake valve deposits in engines utilizing the hydantoin-containing polyether alcohol compounds of the present invention. The process comprises supplying to and combusting or burning in an internal combustion engine a fuel composition comprising a major amount of hydrocarbons in the gasoline boiling range and a minor amount of one or more compounds of Formula I and/or Formula II as described hereinbefore.

By supplying to and combusting or burning the fuel composition in an internal combustion engine, deposits in the induction system, particularly deposits on the tulips of the intake valves, are reduced. The reduction is determined by running an engine with clean induction system components and pre-weighed intake valves on dynamometer test stands in such a way as to simulate road operation using a variety of cycles at varying speeds while carefully controlling specific operating parameters. The tests are run for a specific period of time on the fuel composition to be tested. Upon completion of the test, the induction system deposits are visually rated, the valves are reweighed and the weight of the valve deposits is determined.

Controlling Octane Requirement Increases

The invention further provides a process for controlling octane requirement increases in engines utilizing the hydantoin-containing polyether alcohols of the present invention. The process comprises supplying to and combusting or burning in an internal combustion engine a fuel composition comprising a major amount of hydrocarbons in the gasoline boiling range and a minor amount of one or more compounds of Formula I and/or Formula II as described hereinbefore.

Octane requirement is the maximum octane number of a gasoline that presents trace knock in a given engine within the engine's normal operating range. An increase in octane requirement is generally experienced during mileage accumulation on a new engine. The increase is typically attributed to an increase in engine deposits. Octane requirement increase control is a performance feature that is usually expressed as a comparison of the octane requirement increase developed with a gasoline containing additives (test gasoline) relative to a version of the same gasoline without additives (base gasoline), i.e., the positive difference obtained by subtracting the results of gasoline containing additives from gasoline which does not contain additives.

The test protocol for octane requirement increase control must establish the stable octane requirement of the base gasoline relative to a clean engine. Base gasoline is typically the test gasoline without additives or special treatment; however, it may be gasoline containing additives for a specific comparison.

Octane requirement increase control testing consists of operating an engine assembled with clean combustion chambers and induction system components on a test gasoline to octane stabilization, measuring the octane requirement at regular intervals. The octane requirement increase control is the difference between the stabilized octane requirement of the engine operated on test gasoline and that of the stabilized octane requirement of the engine on base gasoline.

Reduction of Octane Requirement

The invention still further provides a process for reducing octane requirement in engines utilizing the hydantoin-containing polyether alcohols of the present invention. The process comprises supplying to and combusting or burning in an internal combustion engine a fuel composition comprising a major amount of hydrocarbons in the gasoline boiling range and a minor amount of one or more compounds of Formula I and/or Formula II as described hereinbefore.

Octane requirement reduction is the reduction of the octane requirement of an engine by the action of a particular gasoline, usually measured as a decrease from a stabilized octane requirement condition.

Octane requirement reduction is a performance feature that demonstrates a reduction from the established octane requirement of a base gasoline in a given engine. Octane requirement reduction testing consists of operating an engine, which has achieved stable octane requirement using base gasoline, on a test gasoline for approximately 100 hours. Octane measurements are made daily and octane requirement reduction is a reduction of octane requirement from that of base gasoline. Several octane requirement reduction tests may be conducted in a series for fuel to fuel comparison, or test fuel to base fuel comparison, by restabilizing on base fuel between octane requirement reduction tests.

The contribution of specific deposits is determined by removing deposits of interest and remeasuring octane requirement immediately after the engine is warmed to operating temperature. The octane requirement contribution of the deposit is the difference in ratings before and after deposit removal.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

EXAMPLES

Compound Preparation

The hydantoin-containing polyether alcohol compounds used in the following examples were prepared by reacting an initiator with epoxides in the presence of a potassium compound to produce compounds of Formula I and/or Formula II having a weight average molecular weight (MW) from about 600 to about 4000 as measured by gel permeation chromatography (GPC). Rotary evaporation under reduced pressure typically was conducted at a temperature from room temperature to 120° C.

Example 1 (FORMULA I)

Step 1-Preparation of Initiator

A mixture of 5,5-dimethyl hydantoin (128 g, 1.0 mole), ethylene carbonate (88 g, 1 mole) and potassium fluoride (0.0017 mole) was placed into a three-necked round-bottomed flask equipped with a heating mantle, mechanical stirrer, nitrogen inlet-outlet line, thermometer and Dean-Stark Trap. The mixture was heated to 150° C. for 6hours. The progress of the reaction was monitored by the release of $CO_2$ by-products. After the reaction was completed, the product was cooled to room temperature. The product obtained, 5,5dimethyl-hydantoin(2)-ethanol, was used without further purification.

Step 2-Butoxylation of Initiator

A mixture of the initiator of Step 1 (5,5-dimethyl-hydantoin(2)-ethanol, 43 g, 0.25 moles), toluene (15 g) potassium tert-butoxide (0.4 g) was subjected to rotary evaporation under reduced pressure. The resulting product was charged along with 1,2-epoxybutane (457 g, 6.3 moles) into a one liter autoclave reactor equipped with a heating device, temperature controller, mechanical stirrer and water cooling system. The autoclave reactor was sealed, purged of air with nitrogen and then pressurized to 50 psi with nitrogen at room temperature. The mixture was then heated to a temperature of 137° C.–147° C. for 5.5 hours. The autoclave reactor was then cooled to room temperature and excess gas was vented. A final product (493 g of a clear, transparent, light-colored liquid) was obtained after rotary evaporation under reduced pressure, water extraction and rotary evaporation was repeated. GPC analysis showed MW=1390 and a polydispersity of 1.09. The final product contained two butylene oxide backbones.

Example 2 (FORMULA II)

Step 1-Preparation of Initiator

In a three liter round bottom flask equipped with a mechanical stirrer, thermometer and reflux condenser, a mixture of 5,5 dimethyl hydantoin (512 g, 4.0 moles), epichlorohydrin (92.5 g, 2.2 moles), sodium hydroxide (8.8 g, 2.2 moles), ethanol (512 g) and water (322 g) was heated to reflux for six hours. Following the reaction, sodium chloride was filtered off while the mixture was at a temperature of 60° C.–70° C. The filtrate was evaporated to dryness and the residue was recrystallized from water to give 378 g of 1,3-bis (5,5'-dimethyl hydantoinyl-3')-propan-2-ol with a melting point of 189°–190° C.

Step 2-Butoxylation of Initiator

The initiator of Step 1 (1,3-bis (5,5'-dimethyl hydantoinyl-3')-propan-2-ol, 58 g, 0.19 moles), 1,2-epoxybutane (242 g, 3.4 moles), potassium tert-butoxide (1.7 g) and toluene (100 g) was charged directly into a one liter autoclave reactor equipped with a heating device, temperature controller, mechanical stirrer and water cooling system. The autoclave reactor was sealed, purged of air with nitrogen and then pressurized to 50 psi with nitrogen at room temperature. The mixture was then heated to a temperature of 132° C–142° C. for 10 hours. The autoclave reactor was then cooled to room temperature and excess gas was vented. The crude product was subjected to rotary evaporation under reduced pressure, extracted with water and then subjected to rotary evaporation again to remove impurities. A final light-yellow transparent liquid product (240 g) was obtained. GPC analysis showed MW=1200 and a polydispersity of 1.05.

Example 3 (FORMULA II)

The initiator produced in Step 1 of Example 2 (1,3-bis (5,5'-dimethyl hydantoinyl-3')-propan-2-ol, 62 g, 0.20 mole), 1,2-epoxybutane (438 g, 6.1 moles), potassium tert-butoxide (2.9 g) and toluene (50 g) was charged directly into a one liter autoclave reactor equipped with a heating device, temperature controller, mechanical stirrer and water cooling system. The autoclave reactor was sealed, purged of air with nitrogen and then pressurized to 50 psi with nitrogen at room temperature. The mixture was heated to a temperature of 137° C.–142° C. for seven hours. The autoclave reactor was then cooled to room temperature and excess gas was vented. The crude product was subjected to rotary evaporation under reduced pressure, extracted with water and then subjected to rotary evaporation again. A light brown liquid product (447 g) having a higher molecular weight that of Example 2 was obtained. GPC analysis indicated MW=1730 and a polydispersity of 1.08. The hydroxy number showed 76 mg KOH/g indicating an average of three hydroxy poly 1,2-epoxybutane chains.

Example 4 (FORMULA I)

1-methyl hydantoin (21.4 g, 0.19 moles), 1,2-epoxybutane (280 g, 3.9 moles), potassium tert-butoxide 43.4 g) and toluene (100 g) was directly charged into a one liter autoclave reactor equipped with a heating device, temperature controller, mechanical stirrer and water cooling system. The autoclave reactor was sealed, purged of air with nitrogen and then pressurized to 50 psi with nitrogen at room temperature. The mixture was heated to a temperature of 129° C.–160° C. for six hours. The autoclave reactor was then cooled to room temperature and excess gas was vented. The crude product was subjected to rotary evaporation under reduced pressure, extracted with water and then subjected to rotary evaporation again. A brown liquid final product (270 g) was obtained. GPC analysis indicated MW=1060 and a polydispersity of 2.03.

Test Results

In each of the following tests, the base fuel utilized comprised either premium unleaded gasoline (PU) (90±octane, [R+M/2]) and/or regular unleaded gasoline (RU) (85–88 octane, [R+M/2]). Those skilled in the art will recognize that fuels containing heavy catalytically cracked stocks, such as most regular fuels, are typically more difficult to additize in order to control deposits and effectuate octane requirement reduction and octane requirement increase control. The hydantoin-containing polyether alcohol compounds utilized were prepared as indicated by Example number and were used at the concentration indicated in ppm by weight. The tests employed are described below and the results of the various tests are set forth in the tables below.

Intake Valve Deposit Tests

Engines from vehicles were installed in dynamometer cells in such a way as to simulate road operation using a cycle of idle, low speed and high speed components while carefully controlling specific operating parameters. Fuels with and without the compounds of Formula I and Formula II were tested in a variety of engines having port fuel injection including, 3.0 L Fords (FORD), 2.3 L Oldsmobiles (OLDS) and 3.1 L Chevrolets (CHEV) to determine the effectiveness of the instant compounds in reducing intake valve deposits ("L" refers to liter). Carbureted 0.359 L Honda generator engines were also utilized to determine the effectiveness of the instant compounds in reducing intake valve deposits.

Before each test, the engine was inspected, the induction system components were cleaned and new intake valves were weighed and installed. The oil was changed and new oil and fuel filters, gaskets and spark plugs were installed.

In all engines except the Honda, the tests were run in cycles consisting of idle, 35 mph and 65 mph for a period of 100 hours unless indicated otherwise. In the Honda engines, the tests were run in cycles consisting of a no load idle mode for one minute followed by a three minute mode with a load at 2200 rpm's for a period of 40 hours unless indicated otherwise. At the end of each test, the intake valves were removed and weighed.

Tables 3 and 4 include data obtained using compounds of the present invention (Formula I and Formula II). All tests of compounds of the present invention were carried out with additive concentrations (the amount of Compound Example # used) of 200 parts per million (ppm) non-volatile matter (nvm). Base Fuel results which have 0 ppm additive are also included for comparison purposes. The base fuels are indicated by the absence of a Compound Example # (indicated in the Compound Example # column by —).

TABLE 3

Intake Valve Deposits in Honda Generator Engines

| Compound Example # | Fuel | Concentration ppm By Wt. | Engine # | Average Deposit Weight (mg) |
|---|---|---|---|---|
| 2 | PU | 200 | H3C | 11.7 |
| — | " | 0 | * | 33.2 |
| 3 | PU | 200 | H3C | 13.3 |
| — | " | 0 | * | 33.2 |
| 4 | RU | 200 | H2C | 35.8 |
| — | " | 0 | ** | 45.9 |
| 2 | RU | 200 | H3C | 48.1 |
| — | " | 0 | *** | 88.1 |

— Indicates the results achieved with base fuel in the absence of any additive compound (0 ppm additive compound).
*Average of 4 test runs using the same base fuel in other Honda Generator Engines.
**Average of 4 test runs using the same base fuel in other Honda Generator Engines.
***Average of 2 test runs in the same base fuel in other Honda Generator Engines.

TABLE 4

Intake Valve Deposits in Various Engines

| Compound Example # | Engine | Fuel | Concentration ppm By Wt. | Avg. Deposit Wt (mg) |
|---|---|---|---|---|
| 1 | 3.0 L FORD | RU | 200 | 232.0 |
| — | 3.0 L FORD | " | 0 | 359.8 |
| 1 | 2.3 L OLDS | RU | 200 | 147.9 |
| — | 3.0 L OLDS | " | 0 | 141.0 |
| 1 | 3.1 L CHEV | PU | 200 | 147.1 |
| — | 3.1 L CHEV | " | 0 | 72.2 |

— Indicates the results achieved with base fuel in the absence of any additive compound (0 ppm additive compound).

What is claimed is:

1. A fuel composition comprising a mixture of a major amount of hydrocarbons in the gasoline boiling range and a minor amount of an additive compound having the formula:

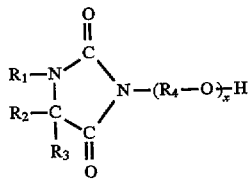

wherein $R_1$ is selected from the group consisting of hydrocarbyl of 1 to 100 carbon atoms, substituted hydrocarbyl of 1 to 100 carbon atoms and polyoxyalkylene alcohol of 2 to 200 carbon atoms; $R_2$ and $R_3$ are each independently selected from the group consisting of hydrogen, hydrocarbyl of 1 to 100 carbon atoms and substituted hydrocarbyl of 1 to 100 carbon or $R_2$ and $R_3$ taken together with the carbon atom to which they are connected form a cyclic group of 4 to 100 carbon atoms; each $R_4$ is independently selected from the group consisting of hydrocarbyl of 2 to 100 carbon atoms and substituted hydrocarbyl of 2 to 100 carbon atoms; x is from 1 to 50; and the weight average molecular weight of the additive compound is at least about 600.

2. The fuel composition of claim 1 wherein said additive compound is present in an amount from about 50 ppm by weight to about 400 ppm by weight based on the total weight of the fuel composition.

3. The fuel composition of claim 2 wherein the weight average molecular weight of the additive compound is from about 800 to about 4000.

4. The fuel composition of claim 3 wherein each $R_4$ is independently selected from hydrocarbyl of 2 to 50 carbon atoms and substituted hydrocarbyl of 2 to 50 carbon atoms.

5. The fuel composition of claim 4 wherein $R_4$ is hydrocarbyl of the formula:

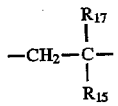

wherein each $R_{17}$ is independently selected from hydrogen, hydrocarbyl of 1 to 18 carbon atoms and substituted hydrocarbyl of 1 to 18 carbon atoms and each $R_{15}$ is independently selected from hydrogen, hydrocarbyl of 1 to 18 carbon atoms and substituted hydrocarbyl of 1 to 18 carbon atoms.

6. The fuel composition of claim 5 wherein $R_2$ and $R_3$ are each independently selected from the group consisting of hydrogen and hydrocarbyl of 1 to 20 carbon atoms.

7. The fuel composition of claim 6 wherein $R_1$ is selected from the group consisting of hydrocarbyl of 1 to 20 carbon atoms and substituted hydrocarbyl of 1 to 20 carbon atoms.

8. The fuel composition of claim 7 wherein $R_1$ is alkyl of 1 to 20 carbon atoms.

9. The fuel composition of claim 8 wherein $R_1$ is alkyl of 1 carbon atom, $R_2$ and $R_3$ are each hydrogen, each $R_{17}$ is hydrogen, each $R_{15}$ is independently selected from hydrogen and alkyl of 1 to 2 carbon atoms and x is from 8 to 26.

10. The fuel composition of claim 6 wherein $R_1$ is polyoxyalkylene of the formula:

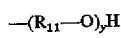

wherein each $R_{11}$ is independently selected from the group consisting of hydrocarbyl of 2 to 100 carbon atoms and substituted hydrocarbyl of 2 to 100 carbon atoms and y is from 1 to 50.

11. The fuel composition of claim 10 wherein each $R_{11}$ is independently selected from the group consisting of hydrocarbyl of 2 to 50 carbon atoms and substituted hydrocarbyl of 2 to 50 carbon atoms.

12. The fuel composition of claim 11 wherein $R_{11}$ is hydrocarbyl of the formula:

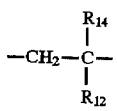

wherein each $R_{14}$ is independently selected from hydrogen, hydrocarbyl of 1 to 18 carbon atoms and substituted hydrocarbyl of 1 to 18 carbon atoms and each $R_{12}$ is independently selected from hydrogen, substituted and hydrocarbyl of 1 to 18 carbon atoms.

13. The fuel composition of claim 12 wherein $R_2$ and $R_3$ are each hydrogen, each $R_{14}$ is hydrogen, each $R_{12}$ is independently selected from the group consisting of hydrogen and alkyl of 1 to 2 carbon atoms, each $R_{17}$ is hydrogen, each $R_{15}$ is independently selected from hydrogen and alkyl of 1 to 2 carbon atoms, x is from 1 to 26 and y is from 1 to 26.

14. The fuel composition of claim 4 wherein $R_4$ is hydrocarbyl of the formula:

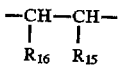

wherein each $R_{16}$ is independently selected from the group consisting of hydrogen, hydrocarbyl of 1 to 18 carbon atoms and substituted hydrocarbyl of 1 to 18 carbon atoms and each $R_{15}$ is independently selected from the group consisting of hydrogen, hydrocarbyl of 1 to 18 carbon atoms and substituted hydrocarbyl of 1 to 18 carbon atoms.

15. The fuel composition of claim 10 wherein $R_{11}$ is hydrocarbyl of the formula:

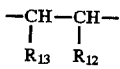

wherein each $R_{13}$ is independently selected from the group consisting of hydrogen, hydrocarbyl of 1 to 18 carbon atoms and substituted hydrocarbyl of 1 to 18 carbon atoms and each $R_{12}$ is independently selected from hydrogen, hydrocarbyl of 1 to 18 carbon atoms and substituted hydrocarbyl of 1 to 18 carbon atoms.

16. A method for decreasing intake valve deposits in an internal combustion engine which comprises burning in said engine a fuel composition comprising a major amount of hydrocarbons in the gasoline boiling range and a minor amount of an additive compound having the formula:

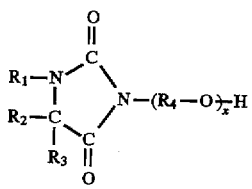

wherein $R_1$ is selected from the group consisting of hydrocarbyl of 1 to 100 carbon atoms, substituted hydrocarbyl of 1 to 100 carbon atoms and polyoxyalkylene alcohol of 2 to 200 carbon atoms; $R_2$ and $R_3$ are each independently selected from the group consisting of hydrogen, hydrocarbyl of 1 to 100 carbon atoms and substituted hydrocarbyl of 1 to 100 carbon or $R_2$ and $R_3$ taken together with the carbon atom to which they are connected form a cyclic group of 4 to 100 carbon atoms; each $R_4$ is independently selected from the group consisting of hydrocarbyl of 2 to 100 carbon atoms and substituted hydrocarbyl of 2 to 100 carbon atoms; x is from 1 to 50; and the weight average molecular weight of the additive compound is at least about 600.

17. The method of claim 16 wherein said additive compound is present in an amount from about 50 ppm by weight to about 400 ppm by weight based on the total weight of the fuel composition.

18. The method of claim 17 wherein the weight average molecular weight of the additive compound is from about 800 to about 4000.

19. The method of claim 18 wherein each $R_4$ is independently selected from hydrocarbyl of 2 to 50 carbon atoms and substituted hydrocarbyl of 2 to 50 carbon atoms.

20. The method of claim 19 wherein $R_4$ is hydrocarbyl of the formula:

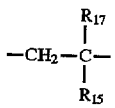

wherein each $R_{17}$ is independently selected from hydrogen, hydrocarbyl of 1 to 18 carbon atoms and substituted hydrocarbyl of 1 to 18 carbon atoms and each $R_{15}$ is independently selected from hydrogen, hydrocarbyl of 1 to 18 carbon atoms and substituted hydrocarbyl of 1 to 18 carbon atoms.

21. The method of claim 20 wherein $R_2$ and $R_3$ are each independently selected from the group consisting of hydrogen and hydrocarbyl of 1 to 20 carbon atoms.

22. The method of claim 21 wherein $R_1$ is selected from the group consisting of hydrocarbyl of 1 to 20 carbon atoms and substituted hydrocarbyl of 1 to 20 carbon atoms.

23. The method of claim 22 wherein $R_1$ is alkyl of 1 to 20 carbon atoms.

24. The method of claim 23 wherein $R_1$ is alkyl of 1 carbon atom, $R_2$ and $R_3$ are each hydrogen, each $R_{17}$ is hydrogen, each $R_{15}$ is independently selected from hydrogen and alkyl of 1 to 2 carbon atoms and x is from 8 to 26.

25. The method of claim 21 wherein $R_1$ is polyoxyalkylene of the formula:

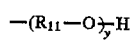

wherein each $R_{11}$ is independently selected from the group consisting of hydrocarbyl of 2 to 100 carbon atoms and substituted hydrocarbyl of 2 to 100 carbon atoms and y is from 1 to 50.

26. The method of claim 25 wherein each $R_{11}$ is independently selected from the group consisting of hydrocarbyl of 2 to 50 carbon atoms and substituted hydrocarbyl of 2 to 50 carbon atoms.

27. The method of claim 26 wherein $R_{11}$ is hydrocarbyl of the formula:

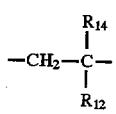

wherein each $R_{14}$ is independently selected from hydrogen, atoms and substituted hydrocarbyl of 1 to 18 carbon atoms and each $R_{12}$ is independently selected from hydrogen, hydrocarbyl of 1 to 18 carbon atoms and substituted hydrocarbyl of 1 to 18 carbon atoms.

28. The method of claim 27 wherein $R_2$ and $R_3$ are each hydrogen, each $R_{14}$ is hydrogen, each $R_{12}$ is independently selected from the group consisting of hydrogen and alkyl of 1 to 2 carbon atoms, each $R_{17}$ is hydrogen, each $R_{15}$ is independently selected from hydrogen and alkyl of 1 to 2 carbon atoms, x is from 1 to 26 and y is from 1 to 26.

29. The method of claim 19 wherein $R_4$ is hydrocarbyl of the formula:

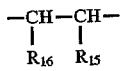

wherein each $R_{16}$ is independently selected from the group consisting of hydrogen, hydrocarbyl of 1 to 18 carbon atoms and substituted hydrocarbyl of 1 to 18 carbon atoms and each $R_{15}$ is independently selected from the group consisting of hydrogen, hydrocarbyl of 1 to 18 carbon atoms and substituted hydrocarbyl of 1 to 18 carbon atoms.

30. The method of claim 25 wherein $R_{11}$ is hydrocarbyl of the formula:

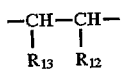

wherein each $R_{13}$ is independently selected from the group consisting of hydrogen, hydrocarbyl of 1 to 18 carbon atoms and substituted hydrocarbyl of 1 to 18 carbon atoms and each $R_{12}$ is independently selected from hydrogen, hydrocarbyl of 1 to 18 carbon atoms and substituted hydrocarbyl of 1 to 18 carbon atoms.

31. A method for reducing octane requirement in an internal combustion engine which comprises burning in said engine a fuel composition comprising a major amount of hydrocarbons in the gasoline boiling range and a minor amount of an additive compound having the formula:

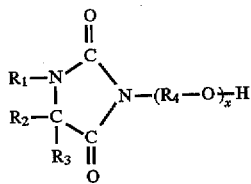

wherein $R_1$ is selected from the group consisting of hydrocarbyl of 1 to 100 carbon atoms, substituted hydrocarbyl of 1 to 100 carbon atoms and polyoxyalkylene alcohol of 2 to 200 carbon atoms; $R_2$ and $R_3$ are each independently selected from the group consisting of hydrogen, hydrocarbyl of 1 to 100 carbon atoms and substituted hydrocarbyl of 1 to 100 carbon or $R_2$ and $R_3$ taken together with the carbon atom to which they are connected form a cyclic group of 4 to 100 carbon atoms; each $R_4$ is independently selected from the group consisting of hydrocarbyl of 2 to 100 carbon atoms and substituted hydrocarbyl of 2 to 100 carbon atoms; x is from 1 to 50; and the weight average molecular weight of the additive compound is at least about 600.

32. A method for controlling the octane requirement increase in an internal combustion engine which comprises burning in said engine a fuel composition comprising a major amount of hydrocarbons in the gasoline boiling range and a minor amount of an additive compound having the formula:

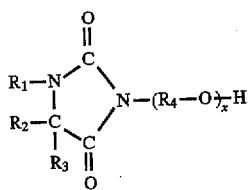

wherein $R_1$ is selected from the group consisting of hydrocarbyl of 1 to 100 carbon atoms, substituted hydrocarbyl of 1 to 100 carbon atoms and polyoxyalkylene alcohol of 2 to 200 carbon atoms; $R_2$ and $R_3$ are each independently selected from the group consisting of hydrogen, hydrocarbyl of 1 to 100 carbon atoms and substituted hydrocarbyl of 1 to 100 carbon or $R_2$ and $R_3$ taken together with the carbon atom to which they are connected form a cyclic group of 4 to 100 carbon atoms; each $R_4$ is independently selected from the group consisting of hydrocarbyl of 2 to 100 carbon atoms and substituted hydrocarbyl of 2 to 100 carbon atoms; x is from 1 to 50; and the weight average molecular weight of the additive compound is at least about 600.

33. A fuel composition comprising a mixture of:

(a) a major amount of hydrocarbons in the gasoline boiling range;

(b) a minor amount of an additive compound having the formula:

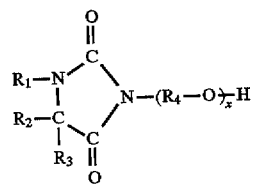

wherein $R_1$ is selected from the group consisting of hydrocarbyl of 1 to 100 carbon atoms, substituted hydrocarbyl of 1 to 100 carbon atoms and polyoxyalkylene alcohol of 2 to 200 carbon atoms; $R_2$ and $R_3$ are each independently selected from the group consisting of hydrogen, hydrocarbyl of 1 to 100 carbon atoms and substituted hydrocarbyl of 1 to 100 carbon or $R_2$ and $R_3$ taken together form a cyclic group of 4 to 100 carbon atoms; each $R_4$ is independently selected from the group consisting of hydrocarbyl of 2 to 100 carbon atoms and substituted hydrocarbyl of 2 to 100 carbon atoms; x is from 1 to 50; and the weight average molecular weight of the additive compound is at least-about 600; and (c) a minor amount of a detergent selected from the group consisting of polyalkylenyl amines, mannich amines, polyalkenyl succinimides, poly(oxyalkylene) carbamates, poly(alkenyl)-N-substituted carbamates and mixtures thereof.

* * * * *